United States Patent [19]

Martindale et al.

[11] Patent Number: 4,795,845

[45] Date of Patent: * Jan. 3, 1989

[54] REGENERATION OF DEHYDROCYCLODIMERIZATION CATALYST

[75] Inventors: David C. Martindale, Roselle; Joseph A. Kocal, Gurnee; Tai-Hsiang Chao, Mt. Prospect, all of Ill.

[73] Assignee: UOP Inc., Des Plaines, Ill.

[*] Notice: The portion of the term of this patent subsequent to Mar. 31, 2004 has been disclaimed.

[21] Appl. No.: 138,187

[22] Filed: Dec. 28, 1987

Related U.S. Application Data

[60] Continuation-in-part of Ser. No. 33,136, Mar. 31, 1987, Pat. No. 4,724,271, which is a continuation-in-part of Ser. No. 871,968, Jun. 9, 1986, Pat. No. 4,654,455, which is a division of Ser. No. 806,984, Dec. 9, 1985, Pat. No. 4,636,483.

[51] Int. Cl.[4] ............................................. C07C 12/02
[52] U.S. Cl. ........................................ 585/415; 502/38
[58] Field of Search ........................... 585/415; 502/38

[56] References Cited

U.S. PATENT DOCUMENTS 4,480,144 10/1984 Smith ................................. 502/52
4,654,455 3/1987 Chao ................................. 585/415

Primary Examiner—Curtis R. Davis
Attorney, Agent, or Firm—Thomas K. McBride; John F. Spears, Jr.; A. Blair Hughes

[57] ABSTRACT

A process for catalytic dehydrocyclodimerization and regeneration of the catalyst. $C_2$ to $C_5$ aliphatic hydrocarbons are reacted to produce aromatics, using a catalyst of a composition especially adapted to minimize deposition of coke on the catalyst. The catalyst is comprised of alumina which contains phosphorus, gallium, and a crystalline aluminosilicate having a silica to alumina ratio of at least 12. The use of this catalyst has resulted in a five-fold reduction in the rate of coke deposition, compared to a conventional dehydrocyclodimerization catalyst. However, the activity of this catalyst once it becomes deactivated is only recovered by burning the coke accumulated upon the deactivated catalyst at catalyst regeneration conditions in the presence of an oxygen-containing gas.

8 Claims, No Drawings

REGENERATION OF DEHYDROCYCLODIMERIZATION CATALYST

CROSS-REFERENCE TO RELATED APPLICATIONS

This application is a continuation-in-part of prior copending application Ser. No. 033,136 filed Mar. 31, 1987, now U.S. Pat. No. 4,724,271 which, in turn, is a continuation-in-part of application Ser. No. 871,968, filed June 9, 1986, now U.S. Pat. No. 4,654,455 which, in turn, is a division of application Ser. No. 806,984 filed Dec. 9, 1985, now U.S. Pat. No. 4,636,483.

FIELD OF THE INVENTION

This invention relates to the field of hydrocarbon conversion processes in which a catalyst is utilized. More specifically, it relates to the regeneration of a specific hydrocarbon conversion catalyst after the catalyst has become deactivated by the deposition of coke thereon.

BRIEF SUMMARY OF THE INVENTION

The present invention is a process for the catalytic dehydrocyclodimerization and regeneration of a zeolite-containing catalyst. $C_2$ to $C_5$ aliphatic hydrocarbons are reacted to produce aromatics, using a catalyst of a composition especially adapted to minimize deposition of coke on the catalyst. The catalyst is comprised of phosphorus-containing alumina, gallium, and a crystalline aluminosilicate having a silica to alumina ratio of at least 12. The use of this catalyst has resulted in a fivefold reduction in the rate of coke deposition, compared to a conventional dehydrocyclodimerization catalyst. However, the activity of this catalyst is significantly reduced over time by the deposition of coke thereon. This activity may be recovered by the combustion of the coke upon the catalyst in the presence of an oxygen-containing gas at catalyst regeneration conditions.

In a broad embodiment, the present invention is a process for the dehydrocyclodimerization of hydrocarbons which comprises contacting a feed stream containing aliphatic hydrocarbons with a catalyst, under dehydrocyclodimerization conditions, where the catalyst is comprised of phosphorus-containing alumina, gallium, and a crystalline aluminosilicate having a silica to alumina ratio of at least 12, where the catalyst becomes deactivated as a result of the deposition of coke thereon as a result of the dehydrocyclodimerization reaction. The catalyst regeneration procedure is comprised of passing an oxygen-containing gas stream across the deactivated catalysts at catalyst regeneration conditions appropriate to combust the coke on the deactivated catalyst and thereby recover catalyst activity. This combustion step can be accomplished with a once-through, or circulating gas stream. The catalyst may be contained in a fixed bed, a moving bed, or the regeneration may be accomplished ex situ.

In a narrower embodiment, the present invention comprises circulating an oxygen-containing gas across a coke deactivated dehydrocyclodimerization catalyst at catalyst regeneration conditions. The catalyst regeneration conditions include a temperature of from 300°–700° C., a pressure of from 1 to 20 atmospheres and a regeneration gas oxygen content of from 0.1 to 23 mole percent. The oxygen in the oxygen-containing regeneration gas is typically supplied by introducing a stream of air into the circulating regeneration gas stream as needed to maintain the desired oxygen level of the regeneration gas.

BACKGROUND OF THE INVENTION

Dehydrocyclodimerization is a reaction where reactants comprising paraffins and olefins containing from 2 to 5 carbon atoms per molecule are reacted in the presence of a catalyst to produce aromatics, with $H_2$ and light ends as by-products. This process is quite different from the more conventional reforming or dehydrocyclization processes where $C_6$ and higher carbon number reactants, primarily paraffins and naphthenes, are converted to aromatics. Aromatics formed in these conventional processes contain the same or a lesser number of carbon atoms per molecule as compared to the reactants from which they were formed, indicating the absence of dimerization reactions. In contrast, the dehydrocyclodimerization reaction results in an aromatic product that always contains more carbon atoms per molecule than the $C_2$ to $C_5$ reactants, thus indicating that the dimerization reaction is a primary step in the process of the present invention.

Typically, a dehydrocyclodimerization reaction is carried out at temperatures in excess of 260° C. using dual-functional catalysts containing an acidic component and a dehydrogenation component. These catalysts include acidic amorphous aluminas which contain metal promoters. Recently, crystalline aluminosilicates have been successfully employed as dehydrocyclodimerization catalysts. Crystalline aluminosilicates, which are generally referred to as zeolites, may be represented by the empirical formula:

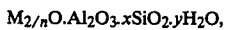

$$M_{2/n}O \cdot Al_2O_3 \cdot xSiO_2 \cdot yH_2O,$$

in which n is the valence of M. M is usually an element of Group I or Group II of the Periodic Table such as sodium, potassium, magnesium, calcium, strontium, or barium, and x is equal to or greater than 2.

Zeolites have skeletal structures which are made up of three dimensional networks of $SiO_4$ and $AlO_4$ tetrahedra, corner linked to each other by shared oxygen atoms. Such zeolites include mordenite and the ZSM variety. In addition to the zeolite component, certain metal promoters and inorganic oxide matrices have been included in dehydrocyclodimerization catalyst formulations. Examples of inorganic oxides include silica, alumina, and mixtures thereof. Metal promoters, such as Group VIII or Group III metals of the Periodic Table, have been used to provide the dehydrogenation functionality. The acidic function can be supplied by the inorganic oxide matrix, the zeolite, or both.

Molecular hydrogen is produced in a dehydrocyclodimerization reaction, as well as aromatic hydrocarbons. For example, reacting a $C_4$ paraffin will yield 5 moles of hydrogen for every mole of aromatic produced. Because the equilibrium concentration of aromatics is inversely proportional to the fifth power of the hydrogen concentration, it is desired to carry out the reaction in the absence of added hydrogen. However, the absence of hydrogen promotes rapid catalyst deactivation, which is caused by carbon formation (coking) on the catalyst surface. This relatively rapid coke deposition makes it necessary to perform the costly and time-consuming catalyst regeneration procedure more frequently. Reducing catalyst coking, thereby increasing catalyst time in service before regeneration is necessary, is an object of this invention.

There are several basic process schemes by which catalyst may be regenerated. Catalyst in the reaction zone may be maintained in continuous use over an extended period of time, up to about a year or more, depending on the quality of the catalyst, the nature of the feedstock, and the processing conditions utilized. Following the extended period of operation, the reactor, or reactors, must be taken out of service while the catalyst is regenerated or replaced with fresh catalyst. Of course, this necessitates shutdown of the hydrocarbon conversion unit.

In another process scheme, known as the swing reactor method, catalyst is regenerated with greater frequency. A multiple fixed bed reactor system is arranged for serial flow of feedstock in such a manner that one reactor at a time can be taken off-stream while the catalyst in that reactor is regenerated or replaced with fresh catalyst. The reactor with fresh catalyst is placed on-stream when another reactor is taken off-stream for the catalyst bed to be regenerated or replaced with fresh catalyst.

In another process scheme, a moving bed reaction zone and regeneration zone are employed. Fresh catalyst particles are supplied to a reaction zone, which may be comprised of several sub-zones, and the particles flow through the zone by gravity. Catalyst is withdrawn from the bottom of the reaction zone and transported to a regeneration zone where a multi-step process is used to recondition the catalyst to restore its full reaction-promoting ability. Catalyst flows by gravity through the various regeneration steps and then is withdrawn from the regeneration zone and supplied to the reaction zone.

Movement of catalyst through the zones is often referred to as continuous, though in practice it is semi-continuous. By semi-continuous movement, it is meant that the catalyst is repeatedly transferred in relatively small amounts at closely spaced points in time. For example, one batch per minute may be withdrawn from the bottom of a reaction zone and withdrawal may take one-half minute, that is, catalyst will flow for one-half minute. If the inventory in the reaction zone is large, the catalyst bed seems to be continuously moving. This method of operation is preferred by many of those skilled in the art. When the moving bed method is used, there is no loss of production while catalyst is regenerated. Also, use of the moving bed method avoids the process upsets of the swing reactor system related to the insertion and removal of a reactors from the process for catalyst regeneration.

Catalyst regeneration is preferably accomplished in a moving bed mode, where catalyst is passed through various treatment zones, rather than practicing the several regeneration stages in a fixed bed of catalyst. Catalyst is passed downwardly through a regeneration vessel by gravity, where it is contacted with a hot oxygen-containing gas stream (known as recycle gas) in order to remove coke which accumulates on surfaces of the catalyst while it is in a hydrocarbon conversion reaction zone. Coke is comprised primarily of carbon but is also comprised of a relatively small quantity of hydrogen. The mechanism of coke removal is oxidation to carbon monoxide, carbon dioxide, and water. The coke content of spent catalyst may be as much as 20% of the catalyst weight, though 0.5 to 7% is a more typical amount.

INFORMATION DISCLOSURE

The prior art recognizes numerous catalyst formulations for the conversion of aliphatic hydrocarbons into aromatic hydrocarbons. Of these catalyst formulations, none embody all of the aspects of the catalytic composition of the present invention nor is it apparent that these prior catalyst formulations have the unique coking tolerance which is characteristic of catalysts of the instant invention. A review of selected prior catalyst formulations may be found in U.S. Pat. No. 4,654,455, which is related to this application.

U.S. Pat. Nos. 4,600,700, 4,463,209, and 4,225,419 deal with catalyst regeneration procedures in which water is beneficial.

U.S. Pat. Nos. 4,477,582 and 4,642,407 teach methods of regeneration of steam-deactivated catalysts.

DETAILED DESCRIPTION OF THE INVENTION

This invention deals with the dehydrocyclodimerization of aliphatic hydrocarbons utilizing a novel catalytic composition comprising phosphorus-containing alumina, a gallium component, and crystalline aluminosilicate having a silica to alumina ratio of at least 12. This catalytic composite yields more aromatics, has a longer life expectancy, and accumulates coke slower than conventional dehydrocyclodimerization catalysts of the prior art. The lower coking tendency increases the economic attractiveness of the dehydrocyclodimerization process by requiring fewer catalyst regeneration cycles, thus increasing the length of time the catalyst can remain on-stream, thereby increasing the production of aromatics per pound of catalyst.

It is believed that the presence of phosphorus-containing alumina is directly responsible for the observed reduced catalyst coke levels. The phosphorus may be combined with the alumina in any acceptable manner known to those skilled in the art. The amount of phosphorus in the catalytic composite can vary over a wide range. A phosphorus to aluminum ratio ranging from about 1:1 to about 1:100 is preferred. A 1:1 molar ratio corresponds to a phosphorus-containing alumina containing 20.5 wt% aluminum and 24.7 wt% phosphorus, while a 1:100 ratio corresponds to 0.6 wt% phosphorus and 52.0 wt% aluminum.

Representative phosphorus-containing compounds which may be utilized in the present invention include $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or a halide. The alkyl groups preferably contain one to four carbon atoms.

Also, primary ($RPH_2$), secondary ($R_2PH$), and tertiary ($R_3P$) phosphines such as butyl phosphine, the tertiary phosphine oxides ($R_3PO$) such as tributylphosphine oxide, the tertiary phosphine sulfides ($R_3PS$), the primary $[RP(O)(OX)_2]$ and secondary $[R_2P(O)OX]$ phosphonic acids such as benzene phosphonic acid, the corresponding sulfur derivatives such as $RP(S)(SX)_2$ and $R_2P(S)SX$, the esters of the phosphonic acids such as dialkyl phosphonate $[(RO)_2P(O)H]$, dialkyl alkyl phosphonates $[(RO)_2P(O)R]$, and alkyl dialkyl-phosphinates [(RO)P(O)R$_2$], phosphinous acids, (R$_2$POX) such as diethylphosphinous acid, primary [(RO)P(OX)$_2$], secondary [(RO)$_2$POX], and tertiary [(RO)$_3$P] phosphites and esters thereof, such as the monopropyl ester, alkyl dialkylphosphinites [(RO)PR$_2$], and dialkyl alkylphosphinite, [(RO)$_2$PR] esters.

Also, corresponding sulfur derivatives such as (RS)$_2$P(S)H, (RS)$_2$P(S)R, (RS)P(S)R$_2$, R$_2$PSX, (RS)P(SX)$_2$, (RS)$_2$PSX, (RS)$_3$P, (RS)PR$_2$ and (RS)$_2$PR. Also, phosphite esters, such as trimethylphosphite, triethylphosphite, diisopropylphosphite, and butylphosphite. Also, pyrophosphites such as tetraethylpyrophosphite.

Also, ammonium hydrogen phosphate, the phosphorus halides such as phosphorus trichloride, alkyl phosphorodichloridites [(RO)PCl$_2$], dialkylphosphorochloridites [(RO)$_2$PCl], dialkyl-phosphinochloridites (R$_2$PCl), alkyl alkylphosphonochloridates [(RO)(R)P(O)Cl], dialkylphosphinochloridates [R$_2$P(O)Cl and RP(O)Cl$_2$]. Also, corresponding sulfur derivatives such as (RS)PCl$_2$, (RS)$_2$PCl, (RS)(R)P(S)Cl, and R$_2$P(S)Cl.

The catalytic composite of the instant invention may be manufactured by any of several techniques known to those skilled in the art. Spheres are a particularly useful shape of the catalytic composite and may be formed by the well-known oil drop method. An exemplary method of manufacture comprises forming an alumina hydrosol by any of the techniques taught in the art, preferably by reacting aluminum metal with aqueous hydrochloric acid, combining the alumina hydrosol with crystalline aluminosilicate zeolite, mixing the resultant alumina zeolite hydrosol with a phosphorus-containing compound, adding a suitable gelling agent, then dispersing droplets of the mixture into an oil bath maintained at an elevated temperature. The droplets of the mixture remain in the oil bath until they set and form hydrogel spheres. The spheres are then withdrawn from the oil bath and typically subjected to an aging, or curing treatment in oil. In a particular process variation, the spheres may be cured in an ammoniacal solution to further improve their physical characteristics. The aged particles are washed in water, dried at a temperature of about 150° to about 250° C., and subjected to a calcination procedure at a temperature of about 450° C. to about 700° C. for a period of about 1 to about 24 hours. This treatment effects conversion of the hydrogel spheres to the desired phosphorus-containing alumina composite. Then gallium is added and a second calcining step is carried out. U.S. Pat. No. 2,620,314 may be consulted for additional information.

The alumina hydrosol is typically prepared by digesting aluminum in aqueous hydrochloric acid and/or aluminum chloride solution at a temperature of from about 80° to about 105° C. The chloride compound concentration of the resulting aluminum chloride solution is reduced by maintaining an excess of aluminum in the reaction mixture. The alumina hydrosol is an aluminum chloride hydrosol which may be, for example, an aluminum oxychloride hydrosol or aluminum hydroxychloride hydrosol. The aluminum chloride hydrosol is prepared with an aluminum to chloride ratio from about 0.70:1 to about 1.5:1 by weight. The crystalline aluminosilicate zeolite is combined with the alumina sol.

The gelling agent is typically a weak base which, when mixed with the hydrosol, will cause the mixture to set to a gel within a reasonable time. Ammonia is often used. Usually, the ammonia is furnished by an ammonia precursor which is added to the hydrosol. The precursor may be hexamethylenetetramine, urea, or mixtures thereof. Other weak basic materials which are substantially stable at normal temperatures but decompose to form ammonia with increasing temperature may be used.

During the above-mentioned aging process, residual ammonia precursor retained in the spheroidal particles continues to hydrolyze and effect further polymerization of the hydrogel, whereby desirable pore characteristics are established. Aging of the hydrogel is accomplished over a period of from about 1 to about 24 hours, preferably in an oil suspending medium, at a temperature of from about 60° to about 150° C. or more, and at a pressure to maintain the water content of the hydrogel spheres in a substantially liquid phase. The aging of the hydrogel can also be carried out in aqueous NH$_3$ solution at about 95° C. for a period up to about 6 hours. Following the aging step the hydrogel spheres may be washed with water containing ammonia.

It may be desirable that, as known to those skilled in the art, the phosphorus-containing alumina of the present invention contain minor amounts of other inorganic oxides such as titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria, and the like. These materials may be added to the mixture prior to oil-dropping.

The catalytic composite of the present invention contains a gallium component, which may be present in any form, including the elemental metal, oxide, hydroxide, halide, oxyhalide, aluminate, or which may be in chemical combination with one or more of the other ingredients of the catalytic composite. Although it is not intended to restrict the present invention by this explanation, it is believed that the best results are obtained when the gallium component is present in the composite in the zero valency state. The gallium component can be used in any amount which is catalytically effective with good results obtained, on an elemental basis, with about 0.1 to about 5% gallium by weight of the total catalytic composite. Best results are ordinarily achieved with about 0.5 to 1 wt% gallium. Although not a necessary condition of the present invention, it is believed that a substantial portion of the gallium present in the catalyst composite is located in and/or on the crystalline aluminosilicate component.

Gallium may be incorporated into the catalytic composite in any suitable manner known to the art which results in a relatively uniform dispersion of the gallium, such as ion exchange, cogelation, or impregnation either after, before, or during the compositing of the catalyst formulation. It is intended to include within the scope of the present invention all conventional methods for incorporating and simultaneously uniformly distributing a metallic component in a catalytic composite. The particular method of incorporation used is not deemed to be an essential feature of the present invention. A preferred method of incorporating the gallium involves ion exchange of the crystalline aluminosilicate with a soluble decomposable compound of gallium, such as gallium tribromide, gallium perchlorate, gallium trichloride, gallium hydroxide, gallium nitrates, gallium oxalate, and the like.

Crystalline aluminosilicate zeolites with silica to alumina ratios of at least 12 are used in the present catalytic composite. A preferred zeolite group is known as the ZSM variety. It is most preferred that ZSM-5 be utilized as the crystalline aluminosilicate component of the present invention, but ZSM-8, ZSM-11, ZSM-12, and ZSM-35 may be used. These ZSM type zeolites are generally prepared by crystallizing a mixture containing a source of alumina, a source of silica, a source of alkali metal, water, and a tetraalkylammonium compound or its precursors. Of course, other crystalline aluminosilicates which meet the silica to alumina ratio criteria may be used, such as faujasites, L-type, mordenites, omega-type, and the like. The relative proportions of the crystalline aluminosilicate zeolite and the other components of the catalytic composite vary widely, with the zeolite content ranging from about 40 percent to about 80 percent by weight and more preferably in the range from about 50 to 70 percent by weight of composite.

The dehydrocyclodimerization conditions which are employed with the catalyst composition of the present invention will vary, depending on such factors as feedstock composition and desired conversion. A range of conditions for the dehydrocyclodimerization of $C_2$–$C_5$ aliphatic hydrocarbons to aromatics includes a temperature from about 350° C. to about 650° C., a pressure from about 1 to about 20 atmospheres, and a liquid hourly space velocity from about 0.2 to about 5 $hr^{-1}$. The preferred process conditions are a temperature in the range from about 400° to about 600° C., a pressure in the range of from about 2 to about 10 atmospheres and a liquid hourly space velocity of between 0.5 to 3.0 $hr^{-1}$. A temperature in the lower end of the range is required for optimum performance when the average carbon number of the feed stream is relatively high and as the average carbon number of the feed decreases the required temperature for optimum conversion increases.

The feed stream to the dehydrocyclodimerization process is comprised of $C_2$–$C_5$ aliphatic hydrocarbon, that is, open, straight, or branched chain hydrocarbons having two, three, four or five carbon atoms per molecule. The hydrocarbons may be saturated or unsaturated. Preferably, the feed stream is comprised of one or more of the following: isobutane, normal butane, isobutene, normal butene, propane, and propylene. The feed stream is contacted with the instant catalytic composite in a reaction zone maintained at dehydrocyclodimerization conditions. The reaction zone may be a fixed bed system or a moving bed system. The catalyst composite of the present invention may be used with a dehydrocyclodimerization catalyst of the prior art in a two-catalyst system.

The feed stream is preheated by any suitable heating means to the desired reaction temperature and then passed into a dehydrocyclodimerization reaction zone containing one or more beds of the instant catalytic composite. The reaction zone may comprise one or more separate reactors with suitable means therebetween to assure that the desired conversion temperature is maintained at the entrance to each reactor. Reactants may be contacted with a catalyst bed in either upward, downward, or radial flow fashion, with the latter being preferred. The reactants may be in the liquid phase, admixed liquid-vapor phase, or a vapor phase when they contact the catalyst, with the best results obtained in the vapor phase. In a multiple bed system, the present catalyst composite may be used in less than all of the beds, with another dehydrocyclodimerization catalyst being used in the remainder of the beds. In a dense-phase moving bed system, catalyst is removed from the bottom of the reaction zone, regenerated, and then returned to the top of the reaction zone.

It is an important aspect of the instant invention that the zeolite-containing hydrocarbon conversion catalyst be regenerable by the oxidation or burning of catalyst deactivating carbonaceous deposits with oxygen or an oxygen-containing gas. By "regenerable", it is meant that at least a portion of the zeolite-containing catalyst's initial activity can be recovered by combusting the coke deposits on the catalyst with oxygen or an oxygen-containing gas. The prior art is replete with catalyst regeneration techniques that may be employed in our process. Some of these regeneration techniques involve chemical methods of increasing the activity of deactivated zeolites. Others are related to processes or methods for regenerating carbon (also known as coke) deactivated catalysts by the combustion of the coke with an oxygen-containing gas stream. For example, U.S. Pat. No. 2,391,327 discloses the regeneration of catalysts contaminated with carbonaceous deposits with a cyclic flow of regeneration gases. U.S. Pat. No. 3,755,961 relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieves. U.S. Pat. No. 4,480,144 relates to the use of a circulating gas to regenerate a coke deactivated zeolite-containing catalyst. The circulating gas is maintained at a low moisture level by purging wet gases from the loop while simultaneously introducing dry gases to the loop. This particular method may be quite advantageous for use in the instant process as a zeolite containing catalyst may be detrimentally affected by moisture. The conditions and methods at which a catalyst may be regenerated by coke combustion with oxygen vary. It is typically desired to perform the coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size in the case of a continuous regeneration process.

Optimum regeneration conditions and methods are those typically disclosed in the prior art as mentioned hereinbefore. To reiterate, catalyst regeneration is typically accomplished at conditions including a temperature range of from 300°–700° C. or higher, a pressure range of from atmospheric to 20 atmospheres, and a regeneration gas oxygen content of from 0.1 to 23.0 mole percent. The oxygen content of the regeneration gas is typically increased during the course of a catalyst regeneration procedure based on catalyst bed outlet temperatures in order to regenerate the catalyst as quickly as possible while avoiding catalyst-damaging process conditions.

Preferred catalyst regeneration conditions include a temperature of from about 300°–600° C., a pressure of about atmospheric to 10 atmospheres, and a regeneration gas oxygen content of from 0.1 to 10.0 mole percent.

Additionally, it is important that the regeneration be accomplished in the presence of an oxygen-containing gas. The oxygen-containing regeneration gas typically is comprised of nitrogen and carbon combustion products such as carbon monoxide, and carbon dioxide to which oxygen in the form of air has been added. However, it is possible that the oxygen can be introduced into the regeneration gas as pure oxygen, or as a mixture of oxygen diluted with some other gaseous component. Air is however the preferred oxygen-containing gas.

It is also an aspect of the instant process that other components such as halogens, acids, hydrogen, and the like disclosed in the prior art may be added to the regeneration gas. Such components are typically added to the regeneration gas during regeneration to promote the activity recovery of the regenerated catalyst.

The regeneration of the instant catalyst is preferably conducted in two steps, a main burn and a clean-up burn. The main burn constitutes the principal portion of the regeneration process. With the molecular oxygen level maintained below about 1.0 mole percent during this main burn, the burning of the coke consumes a major portion of the oxygen so that molecular oxygen in amounts less than that found at the reactor inlet is detected in the gaseous stream at the outlet of the reactor vessel. Near the end of the main burn, oxygen consumption across the catalyst bed will start to decrease, producing an increasing concentration of molecular oxygen at the exit of the reactor. This point in the main burn is referred to as the oxygen breakthrough and essentially marks the end of the main burn. At this point, the clean-up burn portion of the regeneration is initiated by gradually increasing the molecular oxygen concentration in the gas introduced to the catalyst bed. The oxygen concentration can usually be slowly increased to about 7.0 mole percent or greater until the end of the clean-up burn which is indicated by a gradual decline in the temperature at the exit of the catalyst bed until the inlet and outlet temperatures of the catalyst bed merge, i.e. there is essentially no temperature rise across the bed.

The regeneration of the dehydrocyclodimerization catalyst of the instant invention as previously mentioned may be accomplished by a variety of methods known in the prior art. The regeneration may be accomplished using an oxygen-containing gas stream which passes through the spent catalyst at regeneration conditions only once. This is known as a once-through flow of regeneration gas.

In a more preferred method, an oxygen-containing gas is constantly passed across a bed of spent catalyst in a cyclic flow. In this type of gas flow scheme, oxygen is constantly being consumed in the oxidation reaction with the coke on the catalyst. Therefore, oxygen must be added as necessary to the cyclic gas flow to maintain the circulating gas oxygen content at the desired level. This is accomplished by adding small amounts of an oxygen-containing gas, usually air into the circulating gas. Additionally, the system pressure in a circulating gas catalyst regeneration flow scheme would constantly increase due to the addition of the oxygen-containing gas. To avoid this problem, gas is purged from the circulating gas stream as necessary to maintain the system pressure at the desired level.

The regeneration may be accomplished in a fixed bed of catalyst as would occur in a fixed bed, or swing reactor process. The regeneration may also be accomplished in a moving bed of catalyst as would occur in a continuous catalytic regeneration process as described earlier. It is preferred that the regeneration take place in a moving bed catalyst system.

The following example is introduced to further describe the regeneration process of this invention. The example is intended as an illustrative embodiment and should not be considered to restrict the otherwise broad interpretation of the invention as set forth in the claims.

EXAMPLE I

In order to demonstrate the regenerability of a zeolite-containing catalyst when processing a $C_2$-$C_5$ hydrocarbon feedstock, the dehydrocyclodimerization catalyst disclosed in this invention was prepared by the method set forth below. A first solution was prepared by adding phosphoric acid to an aqueous solution of hexamethylenetetramine (HMT) in an amount to yield a phosphorus content of the finished catalyst equal to about 8 wt.%. A second solution was prepared by adding a ZSM-5 type zeolite to enough alumina sol, prepared by digesting metallic aluminum in hydrochloric acid, to yield a zeolite content in the finished catalyst equal to about 67 wt.%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres. These spheres were removed from the oil bath, water washed, air dried, and calcined at a temperature of about 482° C. A solution of gallium nitrate was utilized to impregnate the spheres to achieve a gallium content on the finished catalyst equal to about 1 wt.%. After impregnation, the spheres were calcined a second time, in the presence of steam, at a temperature of about 649° C.

The dehydrocyclodimerization catalyst as prepared above was utilized in a dehydrocyclodimerization pilot plant to convert a propane feed into aromatics. The catalyst was exposed to the propane feedstock and tested for dehydrocyclodimerization performance in a pilot plant using a flow reactor processing a feed comprising 100% propane. The operating conditions used in the pilot plant test comprised a reactor pressure of 1 atmosphere gauge, a liquid hourly space velocity of 0.8 $hr^{-1}$, and a reaction zone inlet temperature of about 538° C. The change in the conversion of the feed over 100 hours of processing was monitored.

Following each pilot plant run, the spent catalyst was regenerated and retested to determine the extent of catalyst activity recovery. The catalyst regeneration method utilized varied over the three tests as summarized in Table I. The catalyst regeneration procedure consisted of placing a bed of the coke deactivated catalyst of varying length in a regeneration reactor and establishing an inert gas flow across the catalyst bed at a gas hourly space velocity of from 3400–4800 $hr^{-1}$. The regeneration temperature and oxygen content were varied over the period of each regeneration based upon the schedule below:

| Hours | Temp. (°C.) | $O_2$, mole % |
|---|---|---|
| 0–1 | 490 | 1 |
| 1–2 | 490 | 2 |
| 2–3 | 490 | 5 |
| 3–4 | 490 | 20 |
| 4–5 | 490–540 | 20 |
| 5–7 | 540 | 20 |

After regeneration, the catalyst was cooled and then reloaded into the dehydrocyclodimerization pilot plant for further pilot plant testing. A summary of the regeneration conditions and pilot plant test results for each test is found in Table I below.

TABLE I

| | Test No. | | |
|---|---|---|---|
| | 1 | 2 | 3 |
| Regeneration | | | |
| Bed Length (m) | 0.28 | 0.013 | 0.05 |
| G.H.S.V. (hr$^{-1}$) | 3400 | 3400 | 4800 |
| Superficial Velocity (m/sec) | 0.28 | 0.013 | 0.05 |
| % Steam Added | 11 | 0 | 0 |
| Pilot Plant Testing | | | |
| C$_3$ Conversion % at Start of Run | 73 | 72 | 69 |
| C$_3$ Conversion % at End of Run | 51 | 45 | 52 |
| C$_3$ Conversion % After Regen. | 69 | 70 | 66 |

It is apparent from the data in Table I that the regeneration of the dehydrocyclodimerization catalyst of the present invention is very effective in recovering a substantial portion of the fresh catalyst activity of the catalyst. This can be seen by comparing the value of the end of run C$_3$ conversion for each catalyst with the C$_3$ conversion value at the start of the run following catalyst regeneration. It can therefore be concluded that the regeneration of the catalyst of the present invention is very important in maximizing the effciency of a process utilizing the catalyst.

What is claimed is:

1. A process for the dehydrocyclodimerization of hydrocarbons which comprises contacting a feed stream containing aliphatic hydrocarbons with a catalyst, under dehydrocyclodimerization conditions, where said catalyst is comprised of phosphorus-containing alumina, gallium, and a crystalline aluminosilicate having a silica to alumina ratio of at least 12, where said catalyst becomes deactivated as a result of the dehydrocyclodimerization reaction, and where the deactivated catalyst is regenerated by contacting the deactivated catalyst with an oxygen-containing regeneration gas at catalyst regeneration conditions.

2. The process of claim 1 further characterized in that the deactivated catalyst is regenerated in the presence of a cyclic flow of oxygen-containing regeneration gas in which at least a portion of the regeneration gas leaving the deactivated catalyst bed is combined with an oxygen-containing gas and recycled back to the deactivated catalyst bed.

3. The process of claim 1 further characterized in that the deactivated catalyst is regenerated in the presence of a once-through flow of an oxygen-containing regeneration gas.

4. The process of claim 1 further characterized in that the deactivated catalyst is contained in a fixed bed.

5. The process of claim 1 further characterized in that the deactivated catalyst is contained in a moving bed of catalyst.

6. The process of claim 1 further characterized in that the regeneration conditions comprise a temperature of from 300°–700° C., a pressure of from atmospheric to 20 atmospheres, and a regeneration gas oxygen content of from 0.10 to 23.0 mole percent.

7. A process for the dehydrocyclodimerization of hydrocarbons which comprises contacting a feed stream containing aliphatic hydrocarbons with a catalyst, under dehydrocyclodimerization conditions, where said catalyst is comprised of phosphorus-containing alumina, gallium, and a crystalline aluminosilicate having a silica to alumina ratio of at least 12, where said catalyst become deactivated as a result of the dehydrocyclodimerization reaction, and where the deactivated catalyst is regenerated by contacting the deactivated catalyst with a cyclic flow of an oxygen-containing regeneration gas at catalyst regeneration conditions including a temperature of from 300°–600° C., a pressure from 1 to 10 atmospheres, and at regeneration oxygen content of from 0.1 to 10.0 mole percent.

8. The process of claim 7 further characterized in that the oxygen of the oxygen-containing gas comes from air.

* * * * *